(12) United States Patent
Sablone (10) Patent No.: US 12,036,101 B2
(45) Date of Patent: Jul. 16, 2024

(54) PROCESS FOR MAKING A REFASTENABLE SIDE SEAM, APPARATUS AND ARTICLE HAVING THAT REFASTENABLE SIDE SEAM

(71) Applicant: Fameccanica.Data S.p.A., San Giovanni Teatino (IT)

(72) Inventor: Gabriele Sablone, San Giovanni Teatino (IT)

(73) Assignee: Fameccanica.Data S.p.A., San Giovanni Teatino Chieti (IT)

( * ) Notice: Subject to any disclaimer, the term of this patent is extended or adjusted under 35 U.S.C. 154(b) by 0 days.

(21) Appl. No.: 18/319,527

(22) Filed: May 18, 2023

(65) Prior Publication Data

US 2023/0293357 A1    Sep. 21, 2023

Related U.S. Application Data

(62) Division of application No. 16/585,020, filed on Sep. 27, 2019, now Pat. No. 11,701,270.

(30) Foreign Application Priority Data

Oct. 1, 2018 (IT) .................. 102018000009005

(51) Int. Cl.
*A61F 13/15* (2006.01)
*A61F 13/49* (2006.01)
*A61F 13/56* (2006.01)
A61F 13/58 (2006.01)
A61F 13/62 (2006.01)

(52) U.S. Cl.
CPC .. *A61F 13/15756* (2013.01); *A61F 13/49015* (2013.01); *A61F 13/56* (2013.01); *A61F 2013/5677* (2013.01); *A61F 2013/586* (2013.01); *A61F 13/622* (2013.01)

(58) Field of Classification Search
CPC .......... A61F 13/15756; A61F 13/49015; A61F 13/56; A61F 13/622; A61F 2013/5677
See application file for complete search history.

(56) References Cited

U.S. PATENT DOCUMENTS

2005/0113793 A1* 5/2005 Bianco ............... A61F 13/15756
604/391
2012/0061015 A1* 3/2012 Lavon ............... A61F 13/49015
156/226

FOREIGN PATENT DOCUMENTS

EP           3257488 A1    12/2017
WO     2015042351 A1     3/2015

OTHER PUBLICATIONS

Search Report dated Apr. 17, 2019. 7 pages.

* cited by examiner

*Primary Examiner* — Vishal I Patel
(74) *Attorney, Agent, or Firm* — RMCK Law Group PLC (57) ABSTRACT

A process and an apparatus for making a refastenable side seam of an hygienic absorbent article efficiently, without the need to remove scrap and which allows refastenable side seams to be obtained which are ergonomic, aesthetically pleasing, easily identifiable by the user and such that they do not reduce the wearability of the article. The disclosure also relates to an hygienic absorbent article provided with at least one refastenable side seam. The disclosure also relates to a process and an apparatus for carrying out one or more operations on elastic panels usable for making an hygienic absorbent article provided with at least one refastenable side seam.

2 Claims, 3 Drawing Sheets fig.1 fig.2 fig.3 fig.4 fig.5 fig.6 fig.7 fig.8 fig.9 fig.10 fig.11 fig.12

PROCESS FOR MAKING A REFASTENABLE SIDE SEAM, APPARATUS AND ARTICLE HAVING THAT REFASTENABLE SIDE SEAM

TECHNICAL FIELD

Embodiments of the present invention relate to a process for making a refastenable side seam of a hygienic absorbent article, such as a diaper, a training pant, an incontinence diaper, a sanitary towel, or other articles intended to absorb bodily fluids.

Here and below, by refastenable side seam it is meant any refastenable seam suitable for connecting two panels of a hygienic absorbent article in a removable manner, said refastenable seam also being called in the sector a "reclosable side seam", or "refastenable side seam".

Embodiments of the present invention also relate to an apparatus for making a refastenable side seam of a hygienic absorbent article, as well as to a hygienic absorbent article having at least one such refastenable side seam.

Embodiments of the present invention also relate to a process for making a panel provided with connecting means constituting a refastenable side seam of a hygienic absorbent article.

Here and below, by panel it is meant a component intended for a hygienic absorbent article which may be part of a chain of articles being formed, may be obtained from the latter, or may be a separate component.

BACKGROUND ART

It is known to make hygienic absorbent articles provided with refastenable side seams from a chain of articles being formed which is advanced along a machine direction, the articles being formed having their longitudinal axis positioned transversely to the machine direction.

That production technique is called "cross direction" and is distinguished from another technique in the sector called "machine direction", in which the hygienic absorbent articles are made while they are advanced with their longitudinal axis parallel to the machine direction.

Possible cross direction implementations provide for the use of a chain of articles being formed comprising two elastic bands which are parallel to and spaced from each other transversely to the machine direction, and a plurality of absorbent bodies associated with the elastic bands orthogonally to the machine direction.

Other cross direction implementations provide for the use of a continuous sheet which is shaped along the path in such a way as to form a chain of articles provided with a plurality of leg openings between which the absorbent bodies of the individual articles are positioned orthogonally to the machine direction.

Depending on the specific cross direction implementation used, it is possible to make the refastenable side seams by applying suitable connecting elements on the chain of articles for each of the articles which it comprises.

The connecting elements may comprise conjugated hook and loop elements, which are also known by the brand name of Velcro® systems, adhesives, or other elements suitable for connecting two portions of an article to each other in a removable manner.

Those connecting elements may be directly associated with a portion of an article or may be associated with another connecting element conjugated thereto, in such a way as to connect two portions of an article to each other in a removable manner.

Once the connecting elements have been applied on the chain of articles, the latter may be folded along an axis parallel to the machine direction, in such a way as to superimpose on each other the portions which will form the waist panels of the individual articles.

In order to separate the articles of the cross-direction chain of articles, it is known to make a plurality of transverse cuts relative to the machine direction, in such a way as to obtain hygienic absorbent articles, each provided with at least one refastenable side seam.

It is known that such operations, besides being particularly complex and subject to errors, involve the presence of scrap which may be removed, or may be kept on the article.

Should the scrap be removed, that would require the presence of special dedicated removal units which, besides complicating the apparatus itself, need frequent maintenance and are also very expensive in both economic and energy terms.

In this context, at the expense of the wearability and aesthetic quality of the articles, some manufacturers are known to prefer keeping the scrap on the articles, thereby avoiding having to remove it.

The articles obtained in this way are not very ergonomic, since at the refastenable side seams the scrap reduces the wearability of the article and also hides the refastenable seam itself which is not easily identified by the user, or by the parent if the article is a diaper.

It is known that if the scrap is kept on the articles it may obstruct, or even damage, some units of the production apparatus which, in the most serious cases, means having to interrupt production in order to restore optimum operating conditions.

Therefore, the need exists to improve and make available a process for making a refastenable side seam of a hygienic absorbent article, a related apparatus, and a hygienic absorbent article comprising that refastenable side seam, which overcome at least one of the disadvantages of the prior art.

One aim of the present invention is to provide an efficient process for making a refastenable side seam of a hygienic absorbent article, which also allows to obtain ergonomic refastenable side seams.

It is also an aim of the present invention to provide an apparatus for making a side seam which does not require the use of a scrap removal unit.

Another aim of the present invention is to provide a hygienic absorbent article provided with refastenable side seams which are aesthetically pleasing, easily identifiable by the user and such that they do not reduce the wearability of the article.

A further aim of the present invention is to provide a process for making a panel provided with connecting means constituting a refastenable side seam of a hygienic absorbent article.

It is also an aim of the present invention to provide a process for carrying out one or more operations, such as cutting operations, in a precise way, avoiding damaging the articles being formed.

Another aim of the present invention is to provide an apparatus for carrying out one or more operations in a precise way, avoiding damaging the articles being formed.

In order to overcome the disadvantages of the prior art and to achieve these and further aims and advantages, the Applicant has studied, experimented and produced the present invention.

DISCLOSURE OF THE INVENTION

The present invention is described and characterized in the independent claims, whilst the dependent claims set out the other characteristics of the present invention or variants of the main solution idea.

According to the above-mentioned aims, the present invention relates to a process for making a refastenable side seam of a hygienic absorbent article suitable for connecting a first elastic panel with a second elastic panel in a removable manner.

According to possible embodiments, the process may provide for:
- supplying the first elastic panel and the second elastic panel each comprising a first layer and a second layer between which at least one elastic element is comprised associated with the first layer and the second layer;
- keeping the first elastic panel and the second elastic panel in extended condition along a respective linear direction;
- fixing at least one connecting element on a respective surface portion of the first elastic panel and/or of the second elastic panel;
- cutting the first elastic panel and/or the second elastic panel so that part of the first elastic panel and/or of the second elastic panel retracts towards the respective surface portion to obtain a respective retracted portion next to the respective surface portion, wherein the connecting element is configured to connect the first elastic panel with the second elastic panel directly, or by means of another connecting element conjugated thereto, so as to make the refastenable side seam.

That aspect allows a refastenable side seam to be obtained without the need to remove the scrap, and which does not compromise the wearability of the hygienic absorbent article, at the same time making the latter aesthetically pleasing.

That solution also allows a refastenable side seam to be obtained which is easily identifiable by a parent, or by the user, since the retracted portion does not hide the connecting elements of the refastenable side seam.

Moreover, the process for making a side seam is simplified compared with the prior art and at the same time is more rapid.

According to possible embodiments, the process provides for the connecting element being able to project beyond the respective surface portion so that the respective retracted portion is at least partially hidden by the connecting element.

According to possible embodiments, the first elastic panel and the second elastic panel may be superimposed, are kept in extended condition along a common linear direction and are cut transversely to the common linear direction.

According to possible embodiments, at least one of the surface portions may be facing towards the outside of the assembly constituted by the superimposed first elastic panel and second elastic panel.

According to possible embodiments, the present invention also relates to an apparatus for making a refastenable side seam of a hygienic absorbent article suitable for connecting a first elastic panel with a second elastic panel in a removable manner, wherein the first elastic panel and the second elastic panel each comprise a first layer and a second layer between which at least one elastic element is comprised associated with the first layer and the second layer.

According to possible embodiments, the apparatus may comprise:
- a supply unit configured to supply the first elastic panel and the second elastic panel, provided with respective means for keeping the first elastic panel and the second elastic panel in extended condition along a respective linear direction;
- an application unit configured to fix at least one connecting element on a respective surface portion of the first elastic panel and/or of the second elastic panel;
- a cutting unit configured to cut the first elastic panel and/or the second elastic panel so that part of the first elastic panel and/or of the second elastic panel retracts towards the respective surface portion, wherein the connecting element is configured to connect the first elastic panel with the second elastic panel directly, or by means of another connecting element conjugated thereto, so as to make the refastenable side seam.

According to possible embodiments, the apparatus provides for the connecting element being able to project beyond the respective surface portion so that the respective retracted portion is at least partially hidden by the connecting element.

That solution allows an apparatus to be provided which does not have a dedicated scrap removal unit, since the retracted portion does not need to be removed.

According to possible embodiments, the present invention also relates to a hygienic absorbent article provided with at least one refastenable side seam suitable for connecting a first elastic panel with a second elastic panel in a removable manner, wherein the first elastic panel and the second elastic panel each comprise a first layer and a second layer between which at least one elastic element is comprised associated with the first layer and the second layer, wherein the first elastic panel and/or the second elastic panel are provided with at least one connecting element fixed on a respective surface portion of the first elastic panel and/or of the second elastic panel, wherein the connecting element is configured to connect the first elastic panel with the second elastic panel directly, or by means of another connecting element conjugated thereto, so as to make the refastenable side seam, and wherein the first elastic panel and/or the second elastic panel comprise a respective retracted portion next to the respective surface portion.

That hygienic absorbent article is provided with refastenable side seams which are aesthetically pleasing, easily identifiable by the user and such that they do not reduce the wearability of the article.

According to possible embodiments, the present invention also relates to a process for making an elastic panel provided with a connecting element for making a refastenable side seam of a hygienic absorbent article.

According to one aspect of the present invention, the process may provide for:
- supplying the elastic panel comprising a first layer and a second layer between which at least one elastic element is comprised associated with the first layer and the second layer;
- keeping the elastic panel in extended condition along a linear direction;
- fixing the connecting element on a surface portion of the elastic panel;
- cutting the elastic panel so that part of the elastic panel retracts towards the surface portion to obtain a retracted portion next to the surface portion.

According to possible embodiments, the connecting element may project beyond the surface portion so that the retracted portion is at least partially hidden by the connecting element.

According to possible embodiments, the elastic panel may be cut transversely to the linear direction.

According to possible embodiments, the present invention also relates to a process for carrying out one or more operations on elastic panels usable for making a hygienic absorbent article provided with at least one refastenable side seam suitable for connecting two of the elastic panels to each other in a removable manner, wherein each of the elastic panels comprises a first layer and a second layer between which at least one elastic element is comprised associated with the first layer and the second layer, wherein at least two of the elastic panels are provided with at least one respective connecting element fixed on a respective surface portion of the respective elastic panel.

According to possible embodiments, the process may provide for keeping the elastic panels superimposed and in extended condition along a linear direction by means of suction, whilst the surface portions are offset relative to each other, in such a way as to carry out one or more operations on at least one of the superimposed elastic panels.

According to possible embodiments, the process may provide for sucking the elastic panels simultaneously from one of the outer surfaces of one of the elastic panels, wherein the elastic panels are breathable to air.

That allows simplification of the apparatus which performs that process, since the suction occurs from a single outer surface of the assembly of superimposed elastic panels.

According to possible embodiments, the process may provide for cutting the elastic panels in such a way that part of each of the elastic panels retracts towards the respective surface portion to obtain a respective retracted portion next to the respective surface portion.

According to possible embodiments, the present invention also relates to an apparatus for carrying out one or more operations on elastic panels usable for making a hygienic absorbent article provided with at least one refastenable side seam suitable for connecting two of the elastic panels to each other in a removable manner, wherein each of the elastic panels comprises a first layer and a second layer between which at least one elastic element is comprised associated with the first layer and the second layer.

According to possible embodiments, the apparatus may comprise:
- a supply unit configured to supply the elastic panels;
- an application unit configured to fix connecting elements on a respective surface portion of the elastic panels;
- a suction unit configured to keep the elastic panels superimposed and in extended condition along a linear direction by means of suction, whilst the surface portions are offset relative to each other, in such a way as to carry out one or more operations on at least one of the superimposed elastic panels.

According to possible embodiments, the suction unit may be configured to suck the elastic panels simultaneously from one of the outer surfaces of one of the elastic panels, wherein the elastic panels are breathable to air.

According to possible embodiments, the apparatus may comprise a cutting unit configured to cut the elastic panels in such a way that part of each of the elastic panels retracts towards the respective surface portion to obtain a respective retracted portion next to the respective surface portion.

According to possible embodiments, the apparatus provides for at least one of the connecting elements being able to project beyond the respective surface portion so that the retracted portion is at least partially hidden by at least one of the connecting elements.

DESCRIPTION OF THE DRAWINGS

These and other features of the present invention will become apparent from the following description of non-limiting embodiments, provided by way of example only, with reference to the accompanying drawings, in which.

For clarity, where possible, identical reference numbers have been used to identify common elements which are identical in the figures. It shall be understood that elements and features of one embodiment may be appropriately incorporated in other embodiments without further explanation.

DESCRIPTION OF EMBODIMENTS OF THE INVENTION

Embodiments described herein, with reference to the figures, relate to a process and to an apparatus 24 for making a refastenable side seam 10 of a hygienic absorbent article 11 suitable for connecting two elastic panels 12 of the article 11 in a removable manner, that is to say, in such a way that the article 11 can be opened/closed, by separating/connecting two elastic panels 12 which are part of the latter.

Here and below, by the term "refastenable side seam" it is meant any refastenable seam, whether it is located in a lateral zone, or in another zone, of the article 11 as is commonly understood in the sector with reference to a "reclosable side seam", or "refastenable side seam".

For the purpose of illustration and without thereby limiting the scope of the present invention, the figures schematically illustrate hygienic absorbent articles 11 which are part of a chain 13 of articles being formed, or are obtained from it.

The chain 13 may comprise two elastic bands 14 with which a plurality of absorbent bodies 15 are associated, or a shaped continuous sheet having a plurality of leg openings between which the absorbent bodies 15 are positioned, or other types of assemblies which define a plurality of articles 11 being formed.

For the purpose of illustration and without thereby limiting the scope of the present invention to a specific type of chain 13 of articles being formed, hereinafter reference will be made to a plurality of elastic panels 12 which are part of the elastic bands 14 and which may be separated from the latter.

According to possible embodiments of the present invention, it shall be understood that any operation carried out on one or more of the elastic panels 12 may occur either while they are part of the chain 13 of articles being formed, or while they are separate from the latter.

Figure 1:
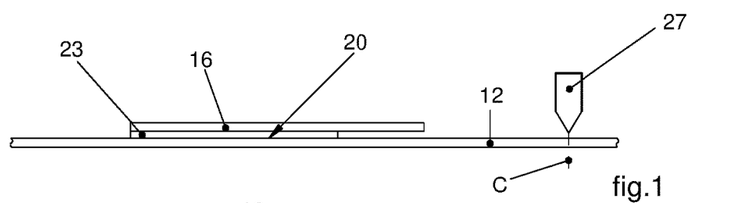
FIGS. 1 and 2 schematically illustrate an elastic panel provided with a connecting element before and after a cut is made according to one possible embodiment of the present invention.
Figure 2:
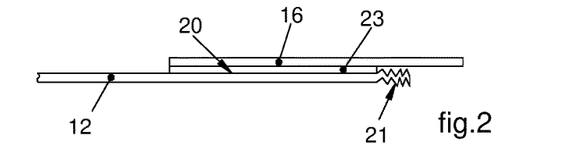

According to possible embodiments, as illustrated in FIGS. 1 and 2, the present invention relates to a process for making an elastic panel 12 provided with a connecting element 16 for making a refastenable side seam 10 of a hygienic absorbent article 11.

According to possible embodiments, the process may provide for:
- supplying an elastic panel 12 comprising a first layer 17 and a second layer 18 between which at least one elastic element 19 is comprised associated with the first layer 17 and the second layer 18;
- keeping the elastic panel 12 in extended condition along a linear direction;
- fixing the connecting element 16 on a surface portion 20 of the elastic panel 12;
- cutting the elastic panel 12 so that part of the elastic panel 12 retracts towards the surface portion 20 to obtain a retracted portion 21 next to the surface portion 20.

According to possible embodiments, the process provides that the connecting element 16 project beyond the surface portion 20 so that the retracted portion 21 is at least partially hidden by the connecting element 16.

According to possible embodiments, the process provides that the elastic panel 12 be cut transversely to the linear direction.

Figure 3:
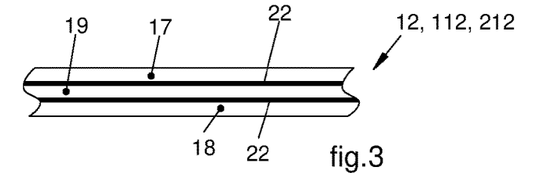
FIG. 3 schematically illustrates a detail of an elastic panel.
Figure 4:
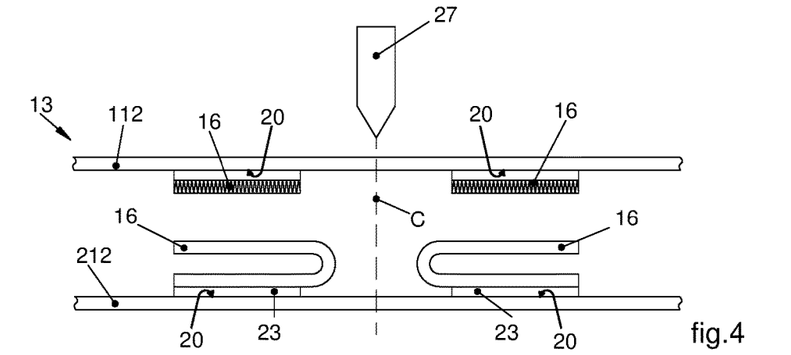
FIGS. 4 and 5 schematically illustrate a first elastic panel and a second elastic panel provided with respective connecting elements before and after a cut is made according to one possible embodiment of the present invention.
Figure 5:
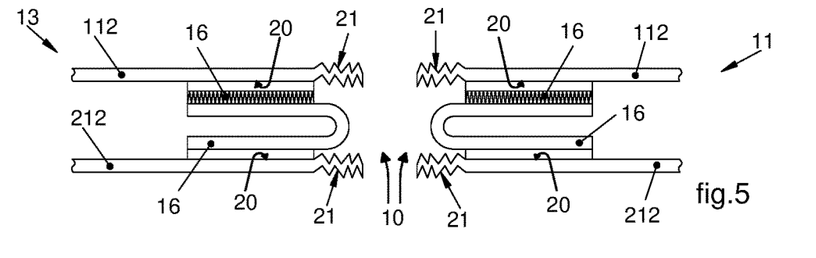
Figure 6:
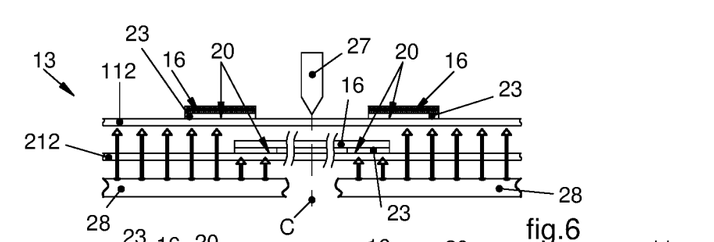
FIGS. 6 and 7 schematically illustrate a first elastic panel and a second elastic panel provided with respective connecting elements before and after a cut is made according to one possible embodiment of the present invention.
Figure 7:
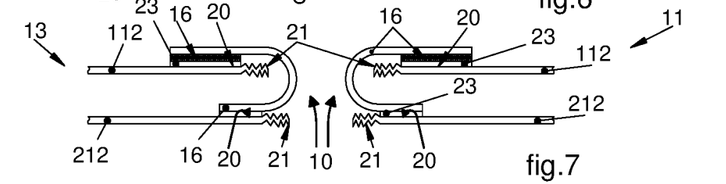
Figure 8:
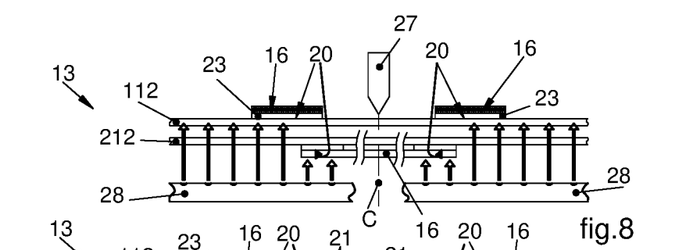
FIGS. 8 and 9 schematically illustrate a first elastic panel and a second elastic panel provided with respective connecting elements before and after a cut is made according to one possible embodiment of the present invention.

According to possible embodiments, the elastic element 19 may be an elastic thread, an elastic tape, or other similar elements, or an elastic layer, breathable at least to air, capable of giving elasticity to the elastic panel 12.

For example, the elastic panel 12 may comprise a plurality of elastic elements 19, whether they are elastic threads, elastic tapes, or combinations thereof, associated with a first layer 17 and a second layer 18 which comprise a non-extendible material, for example a non-woven material. In this example, the composite sheet resulting from the combination of the first layer 17, the second layer 18 and the elastic elements 19 is an elastic panel 12.

According to possible embodiments, the at least one elastic element 19 may be associated with the first layer 17 and with the second layer 18 in extended condition in such a way that the elastic panel 12 in relaxed condition has a length which is less than that which it has in extended condition.

The elasticity provided by the elastic element 19 associated with the first layer 17 and with the second layer 18 in extended condition allows an elastic panel 12 to be obtained which can be suitably processed to obtain one or more retracted portions 21.

According to possible embodiments, the at least one elastic element 19 may be associated with the first layer 17 and with the second layer 18 by gluing in extended condition.

According to possible embodiments, between the elastic element 19 and the first layer 17 and/or between the elastic element 19 and the second layer 18 there may be adhesive zones 22. For example, those adhesive zones 22 may comprise glue, or an adhesive material.

According to possible embodiments, the at least one elastic element 19 may be associated with the first layer 17 and with the second layer 18 by trapping it between them in extended condition by means of a suitable trapping pattern.

That trapping pattern may comprise a plurality of welds suitably positioned relative to the elastic element 19 for locally trapping the latter in extended condition, or relaxed condition.

In this way, the welds not only define the position of the elastic element 19 but also allow local definition of its elastic properties.

According to possible embodiments, the elastic panel 12 may comprise at least one elastic portion.

According to possible embodiments, the elastic portion covers the entire extent of the elastic panel 12.

According to possible embodiments, one of the elastic portions covers most of the extent of the elastic panel 12.

According to possible embodiments, the elastic panel 12 may comprise at least one elastic portion and at least one non-elastic portion, wherein the elastic portion comprises at least one elastic element 19, and the non-elastic portion is not provided with an elastic element 19, or is provided with an inhibited elastic element 19, that is to say, whose elastic properties are impeded, or considerably reduced. For example, the elastic element 19 may be inhibited by suitably trapping parts of it by means of a defined trapping pattern.

Such possible embodiments of an elastic panel 12 may be used to obtain a panel for the hygienic absorbent article 11 having differentiated zones and provided with one or more retracted portions 21.

According to possible embodiments, the connecting element 16 may be fixed on a surface portion 20 of the first layer 17 and/or of the second layer 18 of the elastic panel 12.

According to possible embodiments, the connecting element 16 may be fixed on the surface portion 20 by gluing, or by welding, in such a way as to obtain a connecting layer 23. Fixing the connecting element 16 by welding is advantageous, since there is no need to use glue.

By surface portion 20 it is meant the portion of the elastic panel 12 which is connected to the connecting element 16. Depending on the cases, the surface portion may be connected to part of the connecting element 16, in such a way that a portion of the connecting element 16 is not connected to the elastic panel 12.

According to possible embodiments, the connecting element 16 may comprise a hook element, a loop element suitable for being connected to a conjugated hook element, an adhesive, or other elements suitable for connecting the elastic panels 12 in a removable manner.

For example, the connecting element 16 may be configured to be removably associated with an elastic panel 12 directly, or by means of another connecting element 16.

According to possible embodiments, the connecting element 16 may project beyond the surface portion 20 so that the retracted portion 21 is at least partially hidden by the connecting element 16.

That aspect allows the retracted portion 21 to be at least partially hidden so that, besides not obstructing the refastenable side seam 10, it does not alter the aesthetic appearance and does not in turn hide the connecting elements 16 from the user who intends to open the article 11.

According to possible embodiments, should the retracted portion 21 have a length in relaxed condition that is less than or equal to the projecting portion of the connecting element 16, the retracted portion 21 may be completely hidden by the connecting element 16.

According to possible embodiments, should the retracted portion 21 have a length in relaxed condition that is greater than the projecting portion of the connecting element 16, the retracted portion 21 may be partially hidden by the connecting element 16.

According to possible embodiments, the elastic panel 12 may be cut transversely to the linear direction.

According to possible embodiments, the elastic panel 12 may be cut mechanically, for example with metal blades, or by means of a laser device, or by means of a thermal cutting device.

According to possible embodiments, the present invention also relates to a process for making a refastenable side seam 10 of a hygienic absorbent article 11 suitable for connecting a first elastic panel 112 with a second elastic panel 212 in a removable manner.

For the purpose of illustration and without thereby limiting the scope of the present invention, in the figures the reference numbers 12, 112 and 212 indicate elastic panels which may be identical, or which comprise different components, parts, or properties.

According to possible embodiments, the process may provide for:
- supplying the first elastic panel 112 and the second elastic panel 212 each comprising a first layer 17 and a second layer 18 between which at least one elastic element 19 is comprised associated with the first layer 17 and the second layer 18;
- keeping the first elastic panel 112 and the second elastic panel 212 in extended condition along a linear direction;
- fixing at least one connecting element 16 on a respective surface portion 20 of the first elastic panel 112 and/or of the second elastic panel 212;
- cutting the first elastic panel 112 and/or the second elastic panel 212 so that part of the first elastic panel 112 and/or of the second elastic panel 212 retracts towards the respective surface portion 20 to obtain a respective retracted portion 21 next to the respective surface portion 20, wherein the connecting element 16 is configured to connect the first elastic panel 112 with the second elastic panel 212 directly, or by means of another connecting element 16 conjugated thereto, so as to make the refastenable side seam 10.

According to possible embodiments, the process may provide for keeping the first elastic panel 112 and the second elastic panel 212 in extended condition along a respective linear direction.

According to possible embodiments, the process may provide for keeping the first elastic panel 112 and the second elastic panel 212 in extended condition along a common linear direction.

According to possible embodiments, the process may provide for keeping the first elastic panel 112 and the second elastic panel 212 in extended condition and at least superimposed along a common linear direction.

According to possible embodiments, the process may provide for the cutting the first elastic panel 112 or the second elastic panel 212 along a cutting line C.

In this case, the retracted portion 21 is generated on the elastic panel 112 or 212 which is cut.

Figures 9, 10:
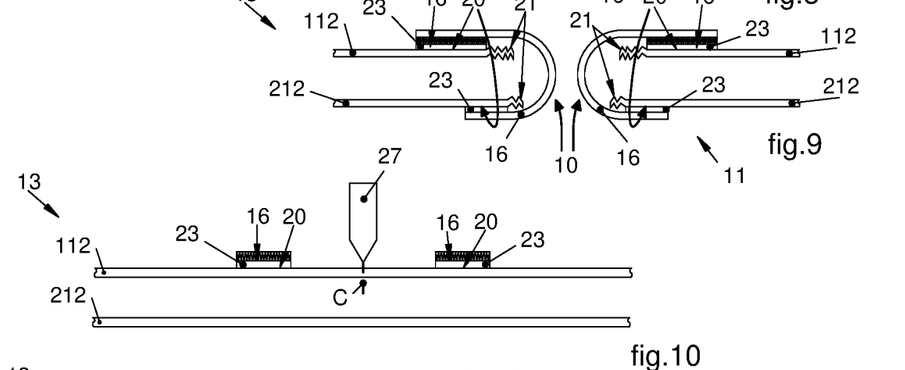
FIGS. 10 to 12 schematically illustrate a first elastic panel provided with connecting elements and a second elastic panel during different steps of a process according to one possible embodiment of the present invention.
Figures 11, 12:
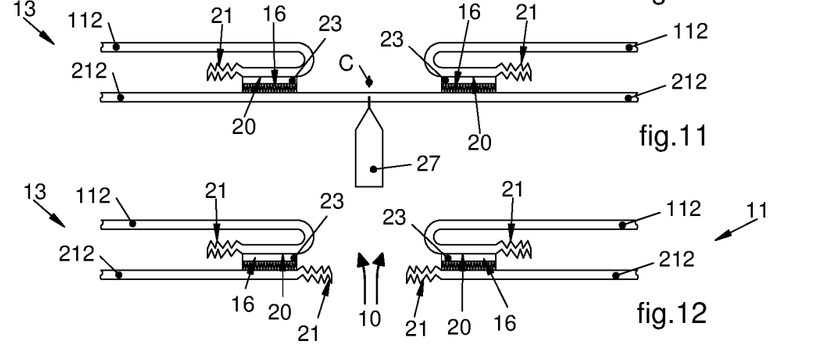

According to possible embodiments, with reference to FIGS. 10 to 12, following cutting of one of the elastic panels 112 or 212 it is possible to carry out further operations either on the elastic panel 112 cut, or on the other elastic panel 212, as well as on both of the elastic panels 112 and 212.

For example, it is possible to suitably fold, or reposition, the edges of the elastic panel 112 which has been cut.

According to possible embodiments, the process may provide for cutting the first elastic panel 112 and the second elastic panel 212 along a common cutting line C. In this case, a respective retracted portion 21 is generated on both of the elastic panels 112 and 212 which have been cut.

According to possible embodiments, the connecting element 16 may project beyond the respective surface portion 20 so that the respective retracted portion 21 is at least partially hidden by the connecting element 16.

According to possible embodiments, the first elastic panel 112 and the second elastic panel 212 are superimposed, are kept in extended condition along a common linear direction and are cut transversely to the common linear direction.

For example, the common linear direction may coincide with one of the linear directions of the first elastic panel 112 and the second elastic panel 212.

That aspect allows both of the elastic panels 112 and 212 to be cut simultaneously, or one after the other, at the same time guaranteeing the precision of the cuts which may be made along cutting lines C located in different zones.

According to possible embodiments, the process may provide that at least one of the surface portions 20 face towards the outside of the assembly constituted by the superimposed first elastic panel 112 and second elastic panel 212.

That embodiment simplifies the operations for application of the connecting elements 18, facilitates the execution of the cuts and at the end of the process allows a refastenable side seam 10 to be obtained which is located far from the user, that is to say, facing outwards towards the side which, in use, is in contact with clothing.

Figure 13:
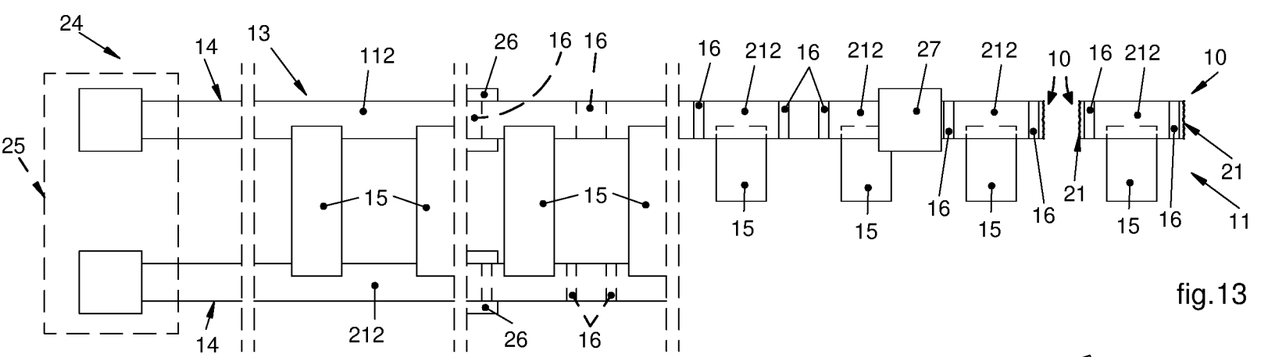
FIG. 13 schematically illustrates part of an apparatus for making hygienic absorbent articles provided with refastenable side seams according to one possible embodiment of the present invention.
Figure 14:
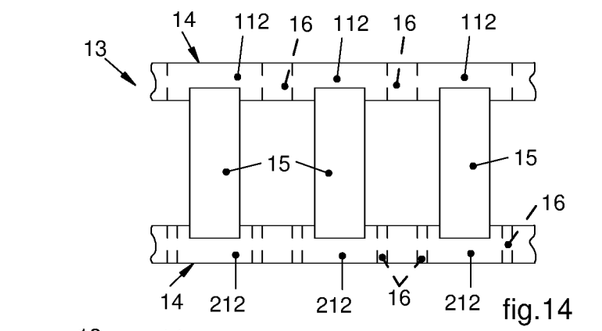
FIGS. 14 and 15 schematically illustrate a portion of a chain of articles being formed in two steps of a process according to one possible embodiment of the present invention.
Figure 15:
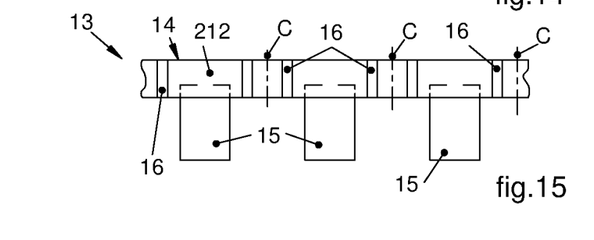

According to possible embodiments, the present invention also relates to an apparatus 24 for making a refastenable side seam 10 of a hygienic absorbent article 11 suitable for connecting a first elastic panel 112 with a second elastic panel 212 in a removable manner, wherein the first elastic panel 112 and the second elastic panel 212 each comprise a first layer 17 and a second layer 18 between which at least one elastic element 19 is comprised associated with the first layer 17 and the second layer 18.

According to possible embodiments, the apparatus 24 may comprise:
- a supply unit 25 configured to supply the first elastic panel 112 and the second elastic panel 212, provided with respective means for keeping the first elastic panel 112 and the second elastic panel 212 in extended condition along a linear direction;
- an application unit 26 configured to fix at least one connecting element 16 on a respective surface portion 20 of the first elastic panel 112 and/or of the second elastic panel 212;

a cutting unit 27 configured to cut the first elastic panel 112 and/or the second elastic panel 212 so that part of the first elastic panel 112 and/or of the second elastic panel 212 retracts towards the respective surface portion 20, wherein the connecting element 16 is configured to connect the first elastic panel 112 with the second elastic panel 212 directly, or by means of another connecting element 16 conjugated thereto, so as to make the refastenable side seam 10.

That solution allows an apparatus 24 to be provided which does not have a dedicated scrap removal unit, since the retracted portion 21 does not need to be removed.

According to possible embodiments, the apparatus 24 may provide that the connecting element 16 project beyond the respective surface portion 20 so that the respective retracted portion 21 is at least partially hidden by the connecting element 16.

According to possible embodiments, the supply unit 25 may comprise specific means for keeping the elastic panels in extended condition for each of the elastic panels 112 and 212. For example, the means for keeping the elastic panels 112 and 212 in extended condition may comprise pulling and/or suction devices. The means for keeping the elastic panels 112 and 212 in extended condition may be configured to keep the first elastic panel 112 and the second elastic panel 212 in extended condition simultaneously.

According to possible embodiments, the apparatus 24 may comprise a plurality of application units 26 each one intended for fixing connecting elements 16 on a respective elastic panel 112 and 212.

According to possible embodiments, the apparatus 24 may comprise a plurality of cutting units 27 each one intended for cutting the respective elastic panels 112 and 212 from the corresponding elastic band 14.

According to possible embodiments, the cutting unit 27 may comprise a mechanical cutting device, for example with a body provided with one or more blades, or a laser cutting device, or a thermal cutting device.

According to possible embodiments, not illustrated, the apparatus 24 may comprise a folding unit configured to fold the chain 13 of articles being formed in such a way as to superimpose the two elastic panels 112 and 212 on each other.

Figure 16:
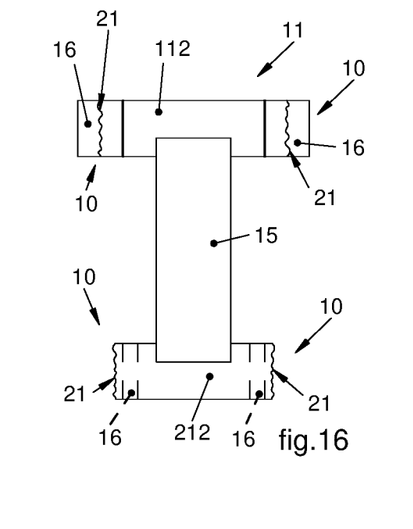
FIG. 16 schematically illustrates a hygienic absorbent article provided with refastenable side seams according to one possible embodiment of the present invention.
Figure 17:
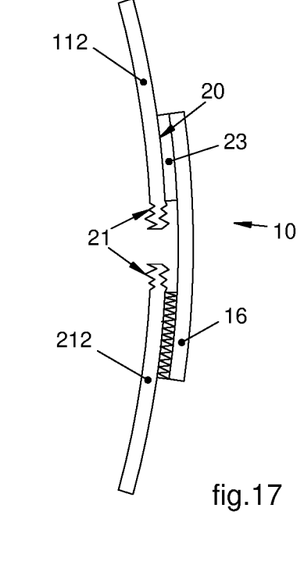
FIG. 17 schematically illustrates a detail of a hygienic absorbent article provided with refastenable side seams according to one possible embodiment of the present invention.

According to possible embodiments, the present invention also relates to a hygienic absorbent article 11 provided with at least one refastenable side seam 10 suitable for connecting a first elastic panel 112 with a second elastic panel 212 in a removable manner, wherein the first elastic panel 112 and the second elastic panel 212 each comprise a first layer 17 and a second layer 18 between which at least one elastic element 19 is comprised associated with the first layer 17 and the second layer 18, wherein the first elastic panel 112 and/or the second elastic panel 212 are provided with at least one connecting element 16 fixed on a respective surface portion 20 of the first elastic panel 112 and/or of the second elastic panel 212, wherein the connecting element 16 is configured to connect the first elastic panel 112 with the second elastic panel 212 directly, or by means of another connecting element 16 conjugated thereto, so as to make the refastenable side seam 10, and wherein the first elastic panel 112 and/or the second elastic panel 212 comprise a respective retracted portion 21 next to the respective surface portion 20.

That hygienic absorbent article 11 is provided with refastenable side seams 10 which are aesthetically pleasing, easily identifiable by the user and such that they do not reduce the wearability of the article 11.

According to possible embodiments, the article 11 may advantageously comprise a connecting element 16 which projects beyond the respective surface portion 20 so that the respective retracted portion 21 is at least partially hidden by the connecting element 16.

According to possible embodiments, the present invention also relates to a process for carrying out one or more operations on elastic panels 112 and 212 usable for making a hygienic absorbent article 11 provided with at least one refastenable side seam 10 suitable for connecting two of the elastic panels 112 and 212 to each other in a removable manner, wherein each of the elastic panels 112 and 212 comprises a first layer 17 and a second layer 18 between which at least one elastic element 19 is comprised associated with the first layer 17 and the second layer 18, wherein at least two of the elastic panels 112 and 212 are provided with at least one respective connecting element 16 fixed on a respective surface portion 20 of the respective elastic panel 112 and 212.

According to possible embodiments, the process provides for keeping the elastic panels 112 and 212 superimposed and in extended condition along a linear direction by means of suction, whilst the surface portions 20 are offset relative to each other, in such a way as to carry out one or more operations on at least one of the superimposed elastic panels 112 and 212.

That aspect allows the precise and controlled performance of one or more operations on at least one of the superimposed elastic panels 112 and 212, controlling them and keeping them in position.

According to possible embodiments, the process may provide for sucking the elastic panels 112 and 212 simultaneously from one of the outer surfaces of one of the elastic panels 112 and 212, wherein the elastic panels 112 and 212 are breathable to air.

That aspect allows both of the elastic panels 112 and 212 to be retained in position simultaneously using the same suction so that one or more operations can be performed with a high precision on one or both of the elastic panels 112 and 212 keeping under consideration the configuration and shape of both of the elastic panels 112 and 212.

That allows to simplify the apparatus 24 which performs that process, since the suction occurs from a single outer surface of the assembly of superimposed elastic panels 112 and 212.

According to possible embodiments, the process may provide for cutting the elastic panels 112 and 212 in such a way that part of each of the elastic panels 112 and 212 retracts towards the respective surface portion 20 to obtain a respective retracted portion 21 next to the respective surface portion 20.

According to possible embodiments, the process may provide that at least one of the connecting elements 16 project beyond the respective surface portion 20 so that the respective retracted portion 21 is at least partially hidden by at least one of the connecting elements 16.

According to possible embodiments, the present invention also relates to an apparatus 25 for carrying out one or more operations on elastic panels 112 and 212 usable for making a hygienic absorbent article 11 provided with at least one refastenable side seam 10 suitable for connecting two of the elastic panels 112 and 212 to each other in a removable manner, wherein each of the elastic panels 112 and 212 comprises a first layer 17 and a second layer 18 between which at least one elastic element 19 is comprised associated with the first layer 17 and the second layer 18.

According to possible embodiments, the apparatus 24 may comprise:
- a supply unit 25 configured to supply the elastic panels 112 and 212;
- an application unit 26 configured to fix connecting elements 16 on a respective surface portion 20 of the elastic panels 112 and 212;
- a suction unit 28 configured to keep the elastic panels 112 and 212 superimposed and in extended condition along a linear direction by means of suction, whilst the surface portions 20 are offset relative to each other, in such a way as to carry out one or more operations on at least one of the superimposed elastic panels 112, 212.

According to possible embodiments, the suction unit 28 may be configured to suck the elastic panels 112 and 212 simultaneously from one of the outer surfaces of one of the elastic panels 112 and 212, wherein the elastic panels 112 and 212 are breathable to air.

According to possible embodiments, the apparatus 24 comprises a cutting unit 27 configured to cut the elastic panels 112 and 212 in such a way that part of each of the elastic panels 112 and 212 retracts towards the respective surface portion 20 to obtain a respective retracted portion 21 next to the respective surface portion 20.

According to possible embodiments, at least one of the connecting elements 16 may project beyond the respective surface portion 20 so that the retracted portion 21 is at least partially hidden by at least one of the connecting elements.

It is clear that the process, the apparatus 24 and the hygienic absorbent article 11 comprising at least one refastenable side seam 10 described above may be modified and/or have parts added, without thereby departing from the scope of the present invention. It is also clear that, although the present invention has been described with reference to several specific examples, a person skilled in the art will certainly be able to make many other equivalent embodiments of the process, the apparatus 24 and the article 11 comprising at least one refastenable side seam 10 which have the features described in the claims and therefore all covered by the scope of protection that they define.

In the claims below, references in brackets are intended only to facilitate reading and must not be considered to be limiting factors as regards the scope of protection of the specific claims.

The invention claimed is:

1. An hygienic absorbent article provided with at least one refastenable side seam suitable for connecting a first elastic panel with a second elastic panel in a removable manner, comprising:
   said first elastic panel and said second elastic panel each including a first layer and a second layer between which at least an elastic element is comprised associated with said first layer and said second layer,
   said first elastic panel and/or said second elastic panel being provided with at least one connecting element fixed on a respective surface portion of said first elastic panel and/or of said second elastic panel,
   said at least one connecting element being configured to connect said first elastic panel with said second elastic panel directly, or by means of another connecting element conjugated thereto, so as to make said refastenable side seam, and
   said first elastic panel and/or said second elastic panel having a respective retracted portion next to the respective surface portion.

2. The article of claim 1, wherein said at least one connecting element projects beyond the respective surface portion so that the respective retracted portion is at least partially hidden by said at least one connecting element.

* * * * *

UNITED STATES PATENT AND TRADEMARK OFFICE
CERTIFICATE OF CORRECTION

| | | |
|---|---|---|
| PATENT NO. | : 12,036,101 B2 | Page 1 of 1 |
| APPLICATION NO. | : 18/319527 | |
| DATED | : July 16, 2024 | |
| INVENTOR(S) | : Gabriele Sablone | |

It is certified that error appears in the above-identified patent and that said Letters Patent is hereby corrected as shown below:

On the Title Page

Item (71) Applicant address information should be listed as:
- Fameccanica.Data S.p.A., San Giovanni Teatino (Chieti), ITALY -

Item (72) Inventor address information should be listed as:
- Gabriele SABLONE, San Giovanni Teatino (Chieti), ITALY -

Signed and Sealed this
Eighteenth Day of March, 2025

Coke Morgan Stewart
*Acting Director of the United States Patent and Trademark Office*